United States Patent [19]

Davis

[11] Patent Number: 4,957,941
[45] Date of Patent: Sep. 18, 1990

[54] ANTI-SPASMDOIC AGENTS HAVING AN ACETYLENIC BOND

[75] Inventor: William M. Davis, Tucson, Ariz.

[73] Assignee: United Pharmaceuticals, Inc., Tucson, Ariz.

[21] Appl. No.: 463,892

[22] Filed: Jan. 9, 1990

Related U.S. Application Data

[63] Continuation of Ser. No. 120,855, Nov. 16, 1987, abandoned; which is a continuation-in-part of Ser. No. 703,318, Feb. 20, 1985, abandoned.

[51] Int. Cl.$^5$ ............... A61K 31/135; A61K 31/395; A61K 31/40; A61K 31/41; A61K 31/435; A61K 31/495; A61K 31/535; A61K 31/54
[52] U.S. Cl. .......................... 514/648; 514/210; 514/211; 514/212; 514/218; 514/226.8; 514/272.5; 514/278.8; 514/231.2; 514/238.8; 514/239.5; 514/255; 514/256; 514/317; 514/359; 514/365; 514/374; 514/408; 514/428; 514/430; 514/431; 514/433; 514/439; 514/648; 540/450; 540/467; 540/470; 540/544; 540/553; 540/575; 540/610; 544/54; 544/58.1; 544/88; 544/158; 544/335; 544/396; 544/397; 546/238; 548/146; 548/215; 548/300; 548/572; 548/950; 558/252; 558/256
[58] Field of Search ............... 540/200, 202, 257, 483, 540/484, 375, 450, 467, 470, 544, 553, 575, 610; 514/210, 211, 212, 218, 226.8, 227.5, 231.2, 238.8, 239.5, 255, 256, 317, 359, 365, 374, 408, 428, 430, 431, 433, 439, 648; 544/54, 58.1, 88, 158, 335, 396, 397; 546/238; 548/146, 215, 300, 572, 950; 558/252, 256, 257

[56] References Cited
FOREIGN PATENT DOCUMENTS
940540 7/1961 United Kingdom .

*Primary Examiner*—William R. Dixon, Jr.
*Assistant Examiner*—David Brunsman
*Attorney, Agent, or Firm*—Austin R. Miller

[57] ABSTRACT

A new class of anti-spasmodic compounds having two branch chains is provided. The compounds have the general formula:

$$\text{Ph}_2\text{C}(\text{Y})(\text{CH}_2)_j\text{—C(=O)—S—(CH}_2)_k\text{—C≡C—(CH}_2)_m\text{—N}\underset{(\text{CH}_2)_p}{\overset{(\text{CH}_2)_n}{<}}\text{X}$$

where
Y is H or OH;
j is an integer from 0 to 4;
k is an integer from 0 to 4, and wherein
m is an integer from 1 to 4;
n is an integer from 1 to 4;
p is an integer from 1 to 4; and
X may be nonexistent or may be O, S, NH or CH$_2$ or salts thereof, but when X is nonexistent the terminal group in which both the n-chain and the p-chain is a methyl group.

$$\underset{\text{carboxylic acid}}{\text{Z—C(=O)—OH}} + \underset{\text{oxalyl chloride}}{\text{Cl—C(=O)—C(=O)—Cl}} \xrightarrow{\text{heat}}$$

$$\underset{\text{acid chloride}}{\text{Z—C(=O)—Cl}} + \text{HCl} + \text{CO}_2 + \text{CO}$$

The reaction was performed under reflux condensation. Following the reaction, which was usually complete within a few hours, the acid chlorides were vacuum distilled and reacted with a thiol compound as described above.

The compounds of this invention are anti-muscarinic agents (cholinergic-muscarinic receptor antagonists) which inhibit the actions of acetylcholine on autonomic effectors innervated by postganglionic cholinergic nerves as well as on smooth muscle that lacks cholinergic innervation. Since a major component of parasympathetic control of smooth muscle occurs via muscarinic receptors, these compounds are effective as modifiers of smooth muscle activity.

Thiphenamil hydrochloride has been shown to decrease spasm of the gastrointestinal tract, biliary tract, ureter and uterus without producing characteristic atropinic side effects on salivary and sweat glands, GI glands, the eye or the cardiovascular system. This invention results in compounds which are as efficacious as thiphenamil hydrochloride, or more so, in relaxing various smooth muscle systems while at the same time demonstrating thiphenamil hydrochloride's lack of associated side-effects.

18 Claims, No Drawings

ANTI-SPASMDOIC AGENTS HAVING AN ACETYLENIC BOND

This application is a continuation of application Ser. No. 120,855, filed 11/16/87, now abandoned, which is a continuation-in-part of U.S. Ser. No. 703,318, filed 2/20/85, now abandoned.

BACKGROUND OF THE INVENTION

1. Field of the Invention

The present invention relates to new pharmaceutical compounds having useful anti-spasmodic properties.

2. Description of the Prior Art

The purpose of an anti-spasmodic drug is to relieve spasms of the smooth muscles. Smooth muscles line most of the visceral organs. The peristalsis and muscular activity of the stomach, intestines, gall bladder, urinary bladder, lung, the uterus, and to a degree the heart are all largely controlled by smooth muscles. Smooth muscles are innervated by the autonomic nervous system. The autonomic nervous system consists of two antagonistic branches—the sympathetic branch and the parasympathetic branch. On all visceral organs except the heart the parasympathetic nerve impulses increase the irritability and tension of the smooth muscles; contrariwise, the sympathetic nerve impulses increase the tension and irritability of the muscles of the heart muscle and relax the smooth muscles of the other visceral organs.

A spasm in a smooth muscle may be due to one of two causes. Either the smooth muscle may be receiving exaggerated impulses from the autonomic nervous system which create violent contractions in the muscle, or the muscle may be intrinsically stimulated into a spasm (most likely from chemical changes in the surround tissue). A spasm due to exaggerated impulses from the parasympathetic branch of the autonomic nervous system may often be corrected by administering atropine (an active alkaloid of belladonna which serves to break a connection between the parasympathetic nerve and the smooth muscle. This ability and effect of atropine is called a "neurotropic effect". A spasm intrinsic in the smooth muscle itself may often be corrected by papaverine (a derivative of opium which is classed as a narcotic). Papaverine has an ability to decrease intrinsically the contractility of smooth muscle; it has the ability to relax smooth muscles directly. This ability and effect of papaverine is called a "musculotropic effect".

In relieving spasms of smooth muscles generally, a musculotropic effect is acknowledged to be superior to a neurotropic effect. A neurotropic effect cannot relieve spasms intrinsic in the smooth muscle itself, while a musculotropic effect, by relaxing and decreasing the irritability and responsiveness of smooth muscle to stimulation from the autonomic nervous system, can help to relieve a smooth muscle spasm even when it is due to exaggerated impulses from the autonomic nervous system.

A clinical difficulty with atropine is that of undesirable side-reactions. Atropine when given in effective doses, serves to break or partly break all the parasympathetic nerve-smooth muscle connections throughout the body. Thus when atropine is given in sufficient dosage to relieve a spasm in a specific visceral organ, such as a gastric or intestinal spasm (the spasm caused by exaggerated nerve impulses from parasympathetic nervous system) undesirable side-actions due to the breaking of the parasympathetic nerve-muscle connections elsewhere in the body may occur. The most easily recognized of these undesirable side reactions are dilation of the pupil and dryness of the mouth, caused by the breaking of the parasympathetic connections to the iris and the saliva producing mechanism respectively.

Atropine is acknowledged to have also a musculotropic effect, but its neurotropic effect is so strong that it cannot be given in greater than minute doses (1/60 to 1/40 grain) without encountering the undesirable side reactions. This dosage is too small to permit a significant musculotropic effect.

U.S. Pat. No. 2,390,555 discloses a class of compounds comprising di-N-substituted aminoethyl esters of diphenylthioacetic acid of the general formula $(C_6H_5)_2$—CH—COS—$CH_2CH_2$—R in which R represents a disubstituted amino radical of either the diethylamino group, the morpholino group or the piperidino group. This patent was based upon the discovery that the thio analogs of certain disubstituted acetic acid esters of aminoalcohols have desirable anti-spasmodic properties. These compounds have proven to be very effective and are widely used as anti-spasmodics without encountering the undesirable side reactions due to excessive neurotropic effect.

U.S. Pat. No. 4,432,977 discloses new uses, especially for the dilation of the smooth muscles of the upper urinary tract, of the compounds disclosed in U.S. Pat. No. 2,390,555.

In *Compte Rendue de la Societe de Biologie*, 140, pp 477–9, (1946) Dupre, Levy and Tchoubar discloses a series of compounds having the formula $(C_6H_5)(R)CH(:O)SCH_2CH_2N(CH_2CH_3)_2$ where R is either a phenyl group, a propyl group, an isopropyl group, a butyl group or an isoamyl groups. These compounds are all disclosed as being spasmolytic agents.

Compounds of the same general formula given above were prepared by Tchoubar and Letellier-Dupre in *Bulletin de la Societe Chimique*, pp 792–4 (1947) where R was a phenyl group, an ethyl group, a propyl group, an isopropyl group, a butyl group, an isoamyl group or hydrogen.

In *Farmakol. i. Tokiskol.*, pp 10–17 (1956), Liberman discloses a class of compounds having the general formula $(C_6H_5)_2CHCOSCH_2CH_2N$—$R_2$, where both R's are the same and are selected from methyl, ethyl, propyl and butyl groups; and a class of compounds having the general formula $(C_6H_5)$—$CH(C_6H_{11})COSCH_2CH_2N$—$R_2$, wherein both R's are the same and are selected from methyl, ethyl, propyl and butyl groups.

C. A. Buehler et al in the *Journal of Medicinal Chemistry*, 6 pp 230–3 (1963) disclose physiologically active compounds of the general formula $R(R')$—$C(OH)$-$COS(CH_2)_2NR''_2$ wherein R and R' are aryl groups.

R. O. Clinton et al in the *Journal of the American Chemical Society*, 68, pp 2076–7 (1946) synthesized a number of dialkyl aminoalkyl diarylthiolacetates including fluorene-9-carbothioic acid, S-[2-diethylaminoethyl]ester.

SUMMARY OF THE INVENTION

A new class of anti-spasmodic compounds is provided having the general formula:

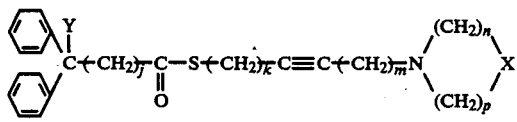

where
Y is H or OH;
j is an integer from 0 to 4;
k is an integer from 0 to 4;
m is an integer from 1 to 4;
n is an integer from 1 to 4;
p is an integer from 1 to 4; and
X may be nonexistent or may be O, S, NH or CH$_2$ or salts thereof, but when X is nonexistent the terminal group in both the n-chain and the p-chain is a methyl group whereby the —N radical is

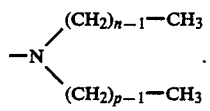

A preferred sub-genus of the compounds having the above described general formula comprises the class of compounds wherein j=0, k=1, m=1 and n, p and X are as above.

The present invention also comprises methods of administering the above-described compounds for, but not limited to, the treatment of patients suffering from pylorospasm in the upper and lower gastrointestinal tract, spasm associated with the gall bladder and common bile duct, as well as diarrhea, the irritable bowel syndrome, ureterospasm, bladder irritation, asthma and emphysema.

DESCRIPTION OF THE PREFERRED EMBODIMENTS

The anti-spasmodic compounds of the present invention are effective in a dosage rnage of from about 0.01 to about 0.15 mg/kilogram of body weight per day. A preferred dosage is in the range of from about 0.015 to about 0.115 mg/kilogram of body weight per day. A still more preferred dosage range is from about 0.03 to about 0.07 mg/kilogram of body weight per day.

The anti-spasmodic compounds of the present invention may be combined with a pharmaceutically acceptable carrier and can be administered orally, typically in tablets of 5 mg active ingredient, total 12 mg, or by intravenous injection, or by topical application.

Because the anti-spasmodic compounds of the present invention generally hydrolyze slowly in water, they are preferably not used as a serum or suspension unless used as a freshly prepared solution. It is possible, however, to encapsulate microspheres of these compounds in the form of a liquid suspension for administration to patients.

As specific examples of the compounds of the present invention, there can be mentioned the following wherein R is

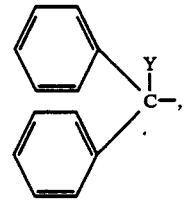

where Y is H or OH:

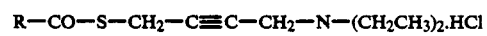

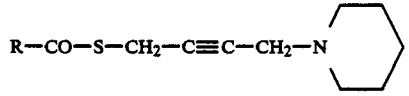

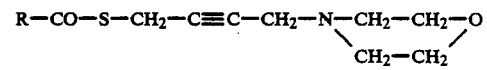

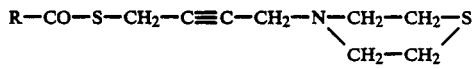

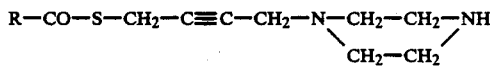

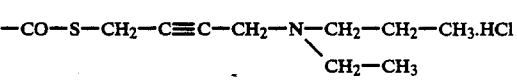

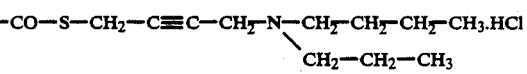

The general reaction used in the synthesis of the anti-spasmodic compounds described in the following examples of the present invention involves the nucleophilic substitution of certain acyl chlorides with certain thiol compounds, such as 4-diethylamino(3-butyryl)ethanethiol. This reaction is illustrated in the following formula, wherein Z represents

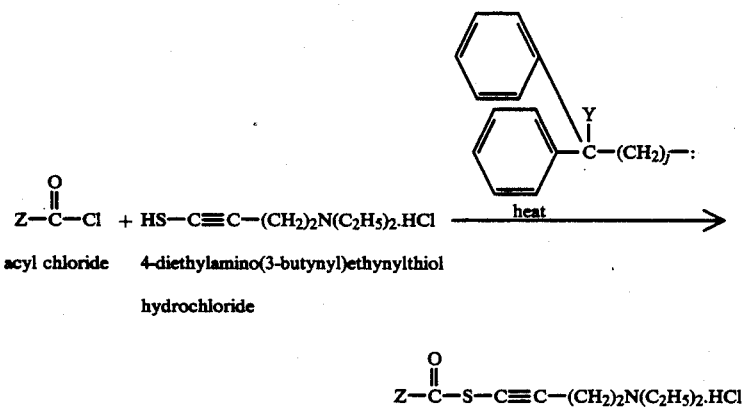

acyl chloride    4-diethylamino(3-butynyl)ethynylthiol hydrochloride

thiol ester hydrochloride 4-diethylamino(3-butynyl)ethynylthiol was purified by re-distillation in vaccuo and nitrogen gas. Subsequently, the thiol was reacted with various acyl chlorides in dichloromethane by combining the two reactants in a 1:1 molar ratio and gently heating under reflux condensation for approximately 1–2 hours. The reaction mixture was then cooled in ice-water until crystallization occurred or, if necessary, in dry ice-ethanol. The crude crystals were harvested by suction filtration and were then recrystallized from an appropriate solvent (e.g. ethyl acetate, acetone, petroleum ether, or dichloromethane).

The desired acyl chlorides may be prepared from the carboxylic acid analogues by reaction with oxalyl chloride as follows:

The following is claimed:

1. A compound of the formula

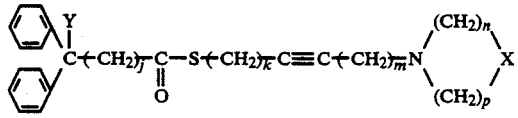

where
Y is H or OH;
j is an integer from 0 to 4;
k is an integer from 0 to 4;
m is an integer from 1 to 4;
n is an integer from 1 to 4;
p is an integer from 1 to 4; and
X may be nonexistent or may be O, S, NH or CH$_2$ or salts thereof, but when X is nonexistent the terminal group in both the n-chain and the p-chain is a methyl group, whereby the —N radical is

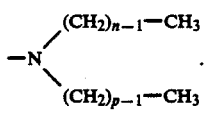

2. The compound as defined in claim 1, wherein j=0, k=1, m=1, n=2, p=2 and X is nonexistent.

3. A method of treating a patient suffering smooth muscle spasm comprising administering to the patient an effective amount of a compound having the formula:

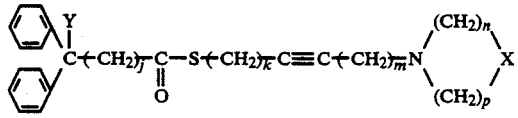

where
Y is H or OH;
j is an integer from 0 to 4;
k is an integer from 0 to 4;
m is an integer from 1 to 4;
n is an integer from 1 to 4;
p is an integer from 1 to 4; and
X may be nonexistent or may be O, S, NH, or CH$_2$ or salts thereof, but when X is nonexistent the terminal group in both the n-chain and the p-chain is a methyl group, whereby the —N radical is

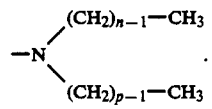

4. The method as defined in claim 3, wherein the compound is administered in a dosage of from 0.01 to about 0.15 mg/kg of body weight per day.

5. The method as defined in claim 3, wherein the compound is administered in a dosage of from about 0.015 to about 0.115 mg/kg of body weight per day.

6. The method as defined in claim 3, wherein the compound is administered in a dosage of from about 0.03 to about 0.07 mg/kg of body weight per day.

7. The method as defined in claim 3, wherein the compound is combined with a pharmaceutically acceptable carrier.

8. The compound as defined in claim 1, wherein j=0, k=2, m=2, n=2, p=2 and X is nonexistent.

9. The compound as defined in claim 1, wherein j=0, k=1, m=1, n=2, p=2 and X is CH$_2$.

10. The compound as defined in claim 1, wherein j=0, k=1, m=1, n=2, p=2 and X is oxygen.

11. The compound as defined in claim 1, wherein j=0, k=1, m=1, n=2, p=2 and X is S.

12. The compound as defined in claim 1, wherein j=0, k=1, m=1, n=2, p=2 and X is NH.

13. The compound as defined in claim 1, wherein j=0, k=1, m=1, n=3, p=2 and X is nonexistent.

14. The compound as defined in claim 1, wherein j=0, k=1, m=1, n=4, p=3 and X is nonexistent.

15. The compound as defined in claim 1, wherein j=0, k=1, m=1, n=1, p=1 and X is nonexistent.

16. The compound as defined in claim 1, wherein j=0, k=1, m=1, n=1, p=1, X is nonexistent and the terminal group in both the n chain and the p chain are bonded together.

17. The compound defined in claim 1, wherein Y is H.

18. The compound defined in claim 1, wherein Y is OH.

* * * * *